United States Patent [19]

Crittenden et al.

[11] Patent Number: 4,719,924
[45] Date of Patent: Jan. 19, 1988

[54] SMALL DIAMETER STEERABLE GUIDEWIRE WITH ADJUSTABLE TIP

[75] Inventors: James F. Crittenden, Hollis, N.H.; Bryan J. White, Lowell, Mass.

[73] Assignee: C. R. Bard, Inc., Murray Hill, N.J.

[21] Appl. No.: 905,622

[22] Filed: Sep. 9, 1986

[51] Int. Cl.⁴ ............................................. A61M 25/00
[52] U.S. Cl. ..................................... 128/772; 128/657; 604/282
[58] Field of Search ............... 128/772, 657; 604/280, 604/282, 95, 170

[56] References Cited

U.S. PATENT DOCUMENTS

| | | | |
|---|---|---|---|
| 3,521,620 | 7/1970 | Cook | 128/772 |
| 3,749,086 | 7/1973 | Kline et al. | 128/772 |
| 3,973,556 | 8/1976 | Fleischhacker et al. | 128/772 |
| 4,080,706 | 3/1978 | Heilman et al. | 128/772 X |
| 4,215,703 | 8/1980 | Willson | 128/772 |
| 4,538,622 | 9/1985 | Samson et al. | 128/657 X |
| 4,545,390 | 10/1985 | Leary | 128/657 X |
| 4,548,206 | 10/1985 | Osborne | 128/772 |
| 4,554,929 | 11/1985 | Samson et al. | 128/657 X |
| 4,619,274 | 10/1986 | Morrison | 128/772 |
| 4,676,249 | 6/1987 | Arenas et al. | 128/772 X |

Primary Examiner—Kyle L. Howell
Assistant Examiner—Angela D. Sykes
Attorney, Agent, or Firm—Wolf, Greenfield & Sacks

[57] ABSTRACT

A small diameter (no greater than about 0.020" diameter) steerable guidewire for cardiovascular surgical procedures or the like is provided with a means by which the curvature at the distal tip of the guidewire can be adjustable by control applied at the proximal end of the guidewire whereby the curve at the distal end of the guidewire can be adjusted without requiring removal of the guidewire from the patient.

15 Claims, 7 Drawing Figures

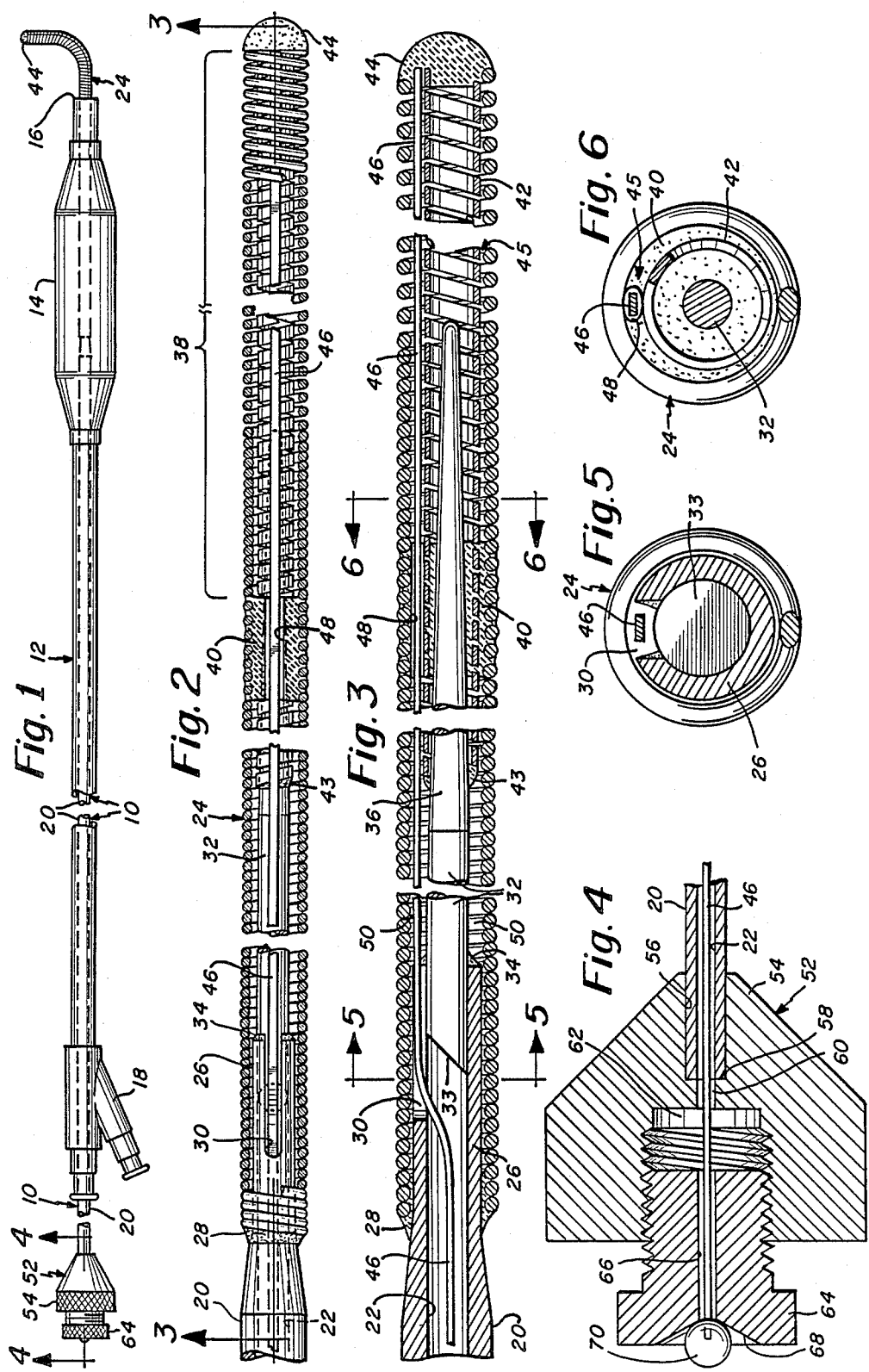

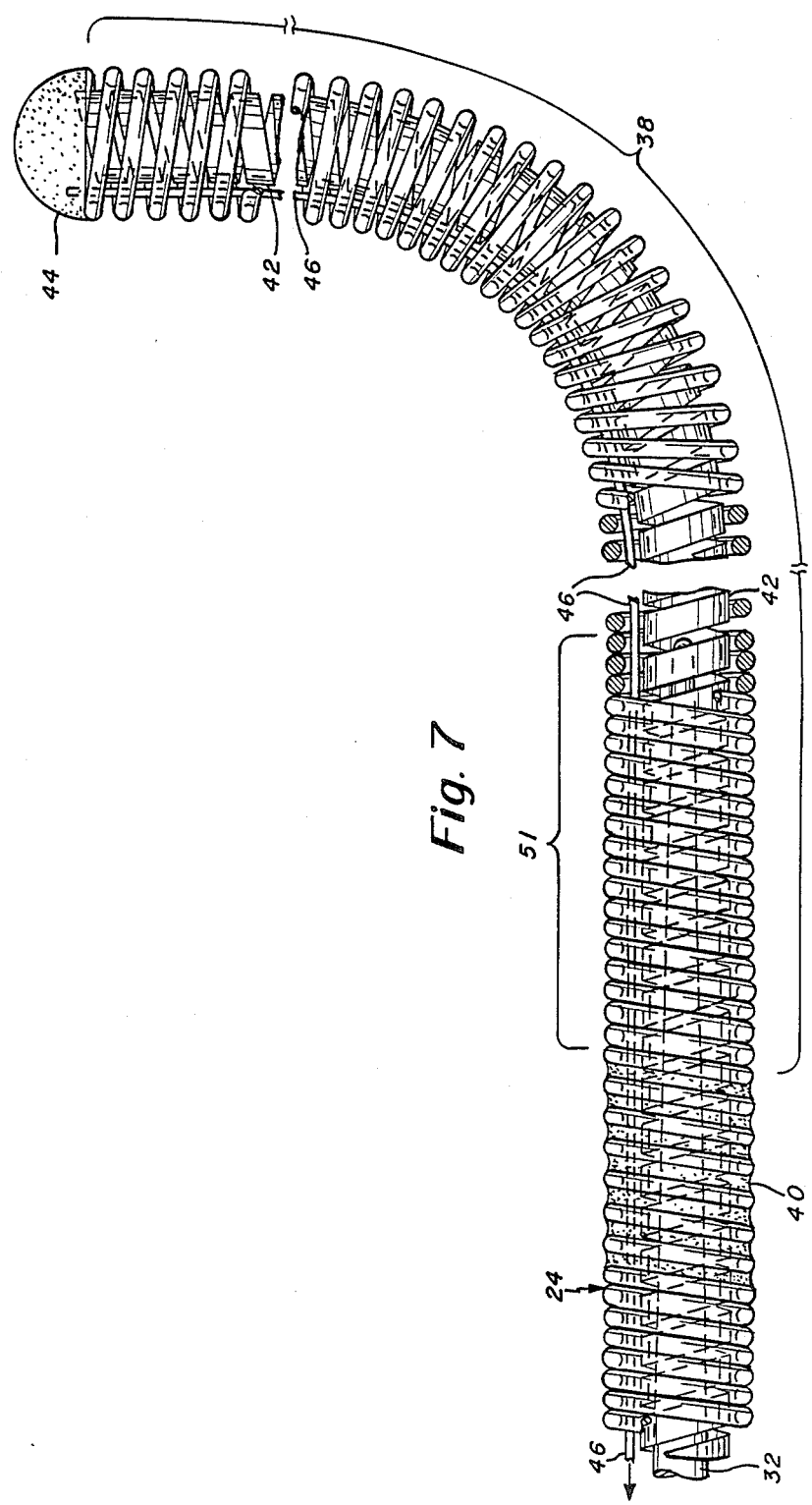

SMALL DIAMETER STEERABLE GUIDEWIRE WITH ADJUSTABLE TIP

FIELD OF THE INVENTION

This invention relates to guidewires used in placement of catheters in cardiovascular surgical procedures and, particularly, to improvements in small diameter steerable guidewires.

BACKGROUND OF THE INVENTION

This invention relates to improvements in the guidewires, particularly guidewires used in small bore blood vessels such as those involved in angioplasty procedures. U.S. Pat. No. 4,545,390 to Leary discloses a small diameter (no greater than about 0.020" in diameter) steerable guidewire which can be advanced and steered into and along very narrow blood vessels to locate the distal end of the guidewire in a precise position in a selected blood vessel branch. Once the guidewire has been so placed, a catheter can be advanced over the guidewire directly to the desired location in the patient's cardiovascular system to enable the catheter to perform its intended function at that location. For example, the invention is particularly useful in coronary angioplasty procedures in which a small diameter balloon dilatation catheter is placed in a narrowed region of a coronary artery so that the balloon may be inflated to widen the lumen of the artery.

U.S. Pat. No. 4,545,390 to Leary discloses a small diameter steerable guidewire which is capable of transmitting from its proximal end to its distal end substantially all of the angular rotation applied to the proximal end. The distal end of the guidewire is adapted to be bent to a set curve by the surgeon before the guidewire is placed in the patient. After the guidewire has been placed in the patient's blood vessel, it may be steered to select between branches of the patient's cardiovascular system by rotating the proximal end of the guidewire to direct selectively the bent distal end of the guidewire to the desired branch. Typically, the guidewire is advanced through the blood vessels while being monitored fluoroscopically.

The steerable guidewire described in the Leary patent was the first small diameter guidewire that could be steered effectively and enabled balloon dilatation procedure to be performed in small diameter distal blood vessels which previously had been unreachable. However, the curve which the surgeon forms at the distal tip of the guidewire, before inserting it into the patient, necessarily involves an approximation by the surgeon as to the degree of curvature best suited for the particular procedure to be performed. Sometimes, after the guidewire has been placed, the degree of bend placed in the distal tip proves to be too great or too little to enable the tip to be steered into a selected blood vessel. Under those circumstances, the physician may have to withdraw the guidewire, reform the bend at its distal tip and then reinsert the guidewire. That complicates and delays the procedure undesirably. It is among the principal objects of the present invention to provide a small diameter steerable guidewire in which the degree of curvature at the distal tip of the guidewire may be adjusted and controlled while the guidewire remains placed in the patient and without requiring removal and manual reshaping of the guidewire.

SUMMARY OF THE INVENTION

The guidewire includes an elongate torsionally rigid shaft formed from a solid walled tube. A slot is formed in the distal end of the tube and a relatively short core wire is attached to and extends distally from the distal end of the tube. The core wire is attached so as to leave a portion of the slot unobstructed. A helically wound outer spring is connected to and encloses the distal region of the tube and all of the core wire. The length of the spring is such that it extends distally beyond the distal tip of the core wire. The distal tip of the spring is provided with a cap. A second, smaller diameter helically wound spring is contained within the outer spring and is connected at its distal end to the cap and at its proximal end to the core wire. A pull wire extends through the full length of the guidewire and is connected at its distal end to the cap at the tip of the spring. The pull wire extends proximally within an annular space between the springs, through an opening in the distal soldered joint, through the open slot in the tube and then through the tube, exiting at the proximal end of the tube. By varying the tension on the pull wire, the degree of curvature at the distal end of the guidewire can be varied controllably.

A tip adjustment mechanism is provided to vary the degree of pull applied to the pull wire and to maintain the pull wire in a fixed position so as to maintain the distal tip of the guidewire in its adjusted "J" configuration while permitting the entire guidewire to be rotated to steer the guidewire. The tip adjustment mechanism includes an enlarged bead which is anchored to the proximal end of the pull wire and also to an axial movable portion of a tip adjustment mechanism which is mounted on the proximal end of the hypo tube.

DESCRIPTION OF THE DRAWINGS

The objects and advantages of the invention will be appreciated more fully from the following further description thereof, with reference to the accompanying drawings wherein:

FIG. 1 is a fragmented side elevation of a catheter with the guidewire of the invention extending through the catheter;

FIG. 2 is an enlarged, fragmented and broken away illustration of the distal region of the guidewire;

FIG. 3 is a sectional illustration of the guidewire as seen along the line 3—3 of FIG. 2;

FIG. 4 is a sectional illustration of the tip adjustment mechanism as seen along the line 4—4 of FIG. 1;

FIG. 5 is a sectional illustration of the guidewire as seen along the line 5—5 of FIG. 3;

FIG. 6 is a sectional illustration of the guidewire as seen along the line 6—6 of FIG. 3; and FIG. 7 is an enlarged illustration of the tip of the guidewire in a curved configuration.

DESCRIPTION OF THE PREFERRED EMBODIMENT

FIG. 1 illustrates the guidewire 10 of the present invention in combination with a balloon dilatation catheter 12. The catheter 12 may be generally of the type described in U.S. Pat. No. 4,545,390 to Leary. The dilatation catheter 12, particular when intended for use in a small artery such as a coronary artery, is relatively slender and, for example, may have an outer diameter of the order of 0.050". The inner dimensions of its lumens, of course, are even smaller and its main lumen may be of the order of 0.022" diameter at its smallest cross-sectional dimension. The catheter has a dilatation balloon 14 at its distal end and a central lumen which is used to deliver liquids such as radiopaque dyes or anticoagulants and also to make distal pressure measurements. The main lumen of the catheter 12 opens at an outlet 16 at the distal tip of the catheter. The catheter also is provided with an inflation lumen (not shown) which is smaller and communicates with the interior of the balloon 14 to inflate and deflate the balloon. The proximal end of the catheter may be provided with a Y-fitting 18 to provide communication at the proximal end of the catheter to each of the central and inflation lumens of the balloon dilatation catheter 12.

As shown in FIGS. 1-3, the guidewire of the present invention includes an elongate main wire 20 which is hollow and is in the form of a solid walled tube having a central lumen 22. The main wire 20 may be formed from stainless steel hypodermic tubing. The main wire 20 extends along the major portion of the length of the guidewire. By way of example, in a guidewire having an overall length of about 180 cm, the main wire 20 may have a length of about 155 cm. The main wire has an outer diameter not greater than about 0.020" and, in the illustrative embodiment of the invention, has a wall thickness of 0.003". The solid walled configuration of the main wire is sufficiently torsionally rigid to transmit substantially fully to the distal end of the wire rotation applied at the proximal end. Thus, the distal end of the guidewire 10 can be caused to rotate in controlled increments to permit steering of the guidewire.

An elongate helical outer spring, indicated generally at 24 is attached to the distal end of the main wire 20. The spring 24 extends along a relatively short portion of the overall length of the guidewire 10. For example, a guidewire having an overall length of about 180 cm may have a spring 24 about 25 cm in length. In the preferred embodiment of the invention, the outer diameter of the spring 24 is not substantially greater than that of the main wire 20 and, preferably, is the same diameter as the main wire 20. The distal end of the main wire 20 is reduced in outer diameter as by drawing the wire lengthwise so that it may fit within the proximal end of the spring 24 in a manner which enables the diameter of the spring 24 to remain substantially the same diameter as the main wire 20.

The proximal end of the spring 24 is connected to the tapered end of the main wire 20 by a brazed joint 28. The tapered distal end 26 of the main wire 20 is provided with a longitudinal slot 30 to permit passage of a pull wire, as will be described. The guide wire 10 also includes a relatively short distal core wire 32 which is secured to and extends distally from the distal end of the main wire 20. In the illustrative embodiment the core wire is not longer than about 20 cm and may have a diameter of about 0.008". The proximal end of the core wire 32 is received in the opening at the distal end 26 of the main wire 20 and is secured thereto with a brazed joint 34. The proximal end of the distal core wire 32 preferably is beveled, to define an upwardly and distally inclined ramp as indicated in FIG. 3 at 33, and is connected so that it terminates short of the blind end of the slot 30 to maintain a portion of the slot 30 open. The bevel at the end 33 of the core wire 32 enables a substantial portion of the slot 30 to be maintained open while providing an increased area of support for the core wire 32 by the distal end 26 of the main wire 20.

The distal end of the distal core wire 32 is tapered along its most distal four to seven centimeters, as suggested at 36. The tapered configuration provides a progressively increasing flexibility along that portion of the guidewire. The tip of the distal core wire 32 terminates short of the distal tip of the spring 24 so that a distal segment 38 of the spring extends beyond the end of the core wire 32. The distal end of the core wire 32 is secured to the spring 24 at a distal brazed joint 40.

The guidewire includes an inner helical spring 42 which is attached at one end to the tapered portion 36 of the core wire 32 and at its distal end to a hemispherical end cap 44 which also is secured to the end of the outer spring 24. The proximal end of the inner spring 42 may be attached to the distal end of the core wire 32 by incorporating it into the distal brazed joint 40. It also may be connected at a brazed joint 43. The inner spring 42 provides an additional margin of protection against breaking and separation of the distal segment 38 of the guidewire from the spring 24 and thus serves as a safety member. The inner or safety spring 42 preferably is wound from rectangular cross-section wire in a helix of opposite direction from that of the outer spring 24. By forming the inner safety spring 42 from a rectangular wire, the outer diameter of the coil may be reduced thus defining in ample somewhat annular space 45 between the outer diameter of the safety spring 42 and the inner diameter of the outer spring 24. As will be described, the annular space 45 (which may be somewhat eccentric as suggested in FIG. 6) receives and provides a channel for a pull wire. The inner safety spring, which is wound in a helix of opposite direction from that of the outer spring 24 provides for additional torsional rigidity at the distal segment 38 of the guidewire but without significantly increasing the flexibility of the segment 38. Winding of the spring 24, 42 in opposite directions also reduces any tendency of the coils of the spring to interlock during operation of the device. As illustrated in FIGS. 2 and 3, the coils of each of the outer spring 24 and inner safety spring 42 may be spaced from each other, as desired, to provide for increased flexibility, as desired.

In accordance with the invention, the configuration of the distal segment 38 of the spring 24 may be controlled to vary the extent to which it is bent or curved without requiring removal of the guidewire from the patient. In accordance with the invention, a pull wire 46, preferably is in the form of a flat stainless steel ribbon having a cross-section of the order of 0.002"×0.003" is provided. It extends the full length of and projects from the proximal end of the guidewire. It is attached at its distal end to the end cap 44, extends proximally through the generally annular region 45 between the inner spring 42 and outer spring 24, then through an aperture 48 formed in the distal joint 40 and then along the annular region 50 defined between the distal core wire 32 and the lumen of the spring 24. The pull wire 46 extends further proximally through the opening defined by the slot 30, into the lumen 22 of the main wire and extends through the lumen of the main wire and exits at the proximal end of the main wire 20. The distal segment 38 normally tends to maintain a straight configuration but can be drawn to a curve of varying degree by pulling on the guidewire 46 to the degree desired.

The springs preferably are formed to maximize the internal diameter of the annular lumens 45, 50 to provide adequate clearance for the pull wire 46 to pass and move freely. In the illustrative embodiment of the invention, the spring 24 may be formed from stainless steel wire having a circular cross-section of 0.002" diameter wound to a spring coil 0.016" diameter. The inner spring 42 may be formed from stainless steel wire having a rectangular cross-section 0.001"×0.003" wound to a coil defining an outer diameter of 0.009" to 0.010". When used with a distal core wire 32 of the order of 0.008" diameter, the remaining diameter clearances of 0.004" and for the annular spaces 45, 50, respectively are adequate for the pull wire which, preferably, also is formed from rectangular wire 0.001"×0.003".

Preferably, at least a portion of the distal segment 38 is expanded somewhat to separate slightly the helical coils one or both of the springs 24, 42. The proportion of separated helical coils in the distal segment 38 affects the radius to which the distal tip can be curved in response to pulling on the pull wire 46. The separated coils define a more flexible configuration in which the coils do not support each other. Thus, the segment of separated coils is more easily bent and will tend to assume a curved or J-shape quite easily in response to tension applied to the pull wire 46. When relatively few of the coils are spaced, pulling on the pull wire 46 will cause them to assume a J-shape while the more proximal unspaced coils in the distal segment will tend to remain straight. Thus, with fewer coils spaced a smaller radius curve is formed. If a greater number of coils in the distal segment are spaced from each other, then the wire will tend to assume a larger radius curve when pull wire 46 is pulled. In the illustrative example of the invention, a portion 51 (see FIG. 7) of the outer spring 24 is formed with the coils close together while the coils in the more distal portion are spaced. As can be seen from FIG. 7, when the wire is pulled, the segment 51 will tend to remain straight, with the curve in the wire being formed in the more distal portion and with a radius slightly smaller than would have been the case had all of the coils, including the segment 51, been spaced.

FIG. 4 shows, in enlarged detail, the tip adjustment mechanism, indicated generally by the reference character 52. The adjustment mechanism 52 includes a cap 54 having a socket 56 which fits over the proximal end of the main wire 20. Socket 56 terminates in a shoulder 58 which abuts the end of the wire 20. An opening 60 extends proximally from the socket 56 and opens into an enlarged internally threaded bore 62. An adjustment screw 64 is threaded into the bore 62. The adjustment screw 64 is provided with a central bore 66 which terminates in a conical depression 68 at the proximal end of the adjustment screw 64. The pull wire 46 thus may extend through the main wire 20, opening 60, bore 62 and bore 66 of the adjustment screw 64. An enlarged ball 70 or similar retention member is securely attached to the proximal end of the pull wire 46 and is seated within the depression 68. Rotation of the adjustment screw is effective to increase or decrease the pull on the pull wire 46. An increased pull on the pull wire draws the distal segment 38 of the guidewire to a curved configuration as suggested in FIG. 7, the extent of curve being dependent on the degree to which the pull wire 46 is pulled. The tip adjustment mechanism 52 may be manipulated to impart the desired degree of curvature to the distal segment 38 and may remain in that position until it is desired to change the curvature.

Thus, from the foregoing, it will be appreciated that the invention provides a small diameter steerable guidewire in which the curve at the distal tip may be controllably adjusted as desired from a straight configuration to a J-configuration while the guidewire is in place in the patient and without requiring removal of the guidewire to adjust the tip. The guidewire improves substantially the facility with which a dilatation procedure may be performed, particularly in small diameter blood vessels having tortuous passages. It should be understood, however, that the foregoing description of the invention is intended merely to be illustrative thereof and that other embodiments and modifications may be apparent to those skilled in the art without departing from its spirit.

Having thus described the invention, what I desire to claim and secure by letters patent is:

1. A steerable small diameter guidewire comprising:
    an elongate solid wall tubular main wire having a proximal end and a distal end;
    an elongate helical coil spring having proximal and distal ends and being connected at its proximal end to the distal end of the main wire and extending distally of the main wire;
    a distal core wire having proximal and distal ends and being connected to and extending distally from the distal end of the main wire, the core wire extending through the lumen of the spring and having a distal tip which terminates short of the distal end of the spring;
    the distal end of the distal core wire being secured to the spring at a location intermediate the ends of the spring thereby to define a distal spring segment extending from the distal end of the core wire to the distal end of the spring, the distal segment being more flexible than the more proximal portions of the guidewire;
    means defining a pull wire opening adjacent to the distal end of the main wire proximally of the proximal end of the distal core wire;
    a pull wire having a proximal end and a distal end, the distal end of the pull wire being secured to the distal end of the spring, the pull wire extending proximally between the core wire and the spring and through the opening into the lumen of the main wire, the pull wire extending proximally through the lumen of the main wire to the proximal end of the main wire;
    whereby the proximal end of the pull wire may be pulled to apply tension to the pull wire thereby to draw at least a portion of the distal segment of the spring into a curved configuration.

2. A steerable small diameter guidewire as defined in claim 1 wherein the outer diameter of the main wire is not substantially greater than about 0.020".

3. A steerable small diameter guidewire as defined in claim 1 further comprising:
    at least some of the coils in the distal spring segment being spaced from each other thereby to define a more flexible portion of the distal segment.

4. A steerable small diameter guidewire as defined in claim 1 wherein the outside diameter of the spring is not substantially greater in diameter than the main wire.

5. A steerable small diameter guide wire as defined in claim 4 further comprising:
    the distal end of the main wire being tapered, said tapered end being received within the proximal end of the spring.

6. A steerable small diameter guidewire as defined in claim 5 further comprising:

said opening in main wire being formed in the tapered end of the main wire.

7. A steerable small diameter guidewire as defined in claim 1 further comprising:
said distal core wire being received within the lumen at the distal end of the tubular main wire and having a beveled proximal end, the bevel being arranged to define a ramp extending distally and toward the pull wire opening.

8. A steerable small diameter guidewire as defined in claim 1 further comprising:
the distal end of the core wire being tapered thereby to define a segment of the guidewire which is of progressively decreasing stiffness.

9. A steerable small diameter guidewire as defined in claim 1 further comprising:
safety means connected between the core wire and the distal end of the helical spring.

10. A steerable small diameter guidewire as defined in claim 9 wherein said elongate helical spring comprises an outer spring and wherein said safety means comprises:
a second helical coil spring of smaller diameter than and contained within the outer helical spring, said outer and inner helical springs being wound in opposite directions;
the pull wire extending in the space defined between the inner and outer springs.

11. A steerable small diameter guidewire as defined in claim 10 further comprising:
at least some of the coils of at least one of said inner and outer springs being spaced from each other thereby to define a more flexible portion of the distal segment.

12. A small diameter steerable guidewire as defined in claim 10 wherein at least one of said springs is formed from wire of rectangular cross-section.

13. A steerable small diameter guidewire as defined in claim 1 further comprising:
said guidewire having proximal and distal ends;
tip adjustment means mounted to the proximal end of the guidewire and being operatively connected to the proximal end of the pull wire, said tip adjustment means being constructed and arranged as to apply and maintain a selected degree of pull to the pull wire.

14. A steerable small diameter guidewire as defined in claim 13 wherein said tip adjustment means comprises:
a cap mounted on the proximal end of the main wire, the cap having an opening formed therethrough to enable the proximal end of the pull wire to extend therethrough;
an adjustment member movably mounted to the cap for movement longitudinally of the guidewire; and
means for connecting the proximal end of the pull wire to the adjustment member whereby the pull applied to the pull wire may be controlled by adjustment in the position of the adjustment member.

15. A guidewire as defined in claim 14 further comprising:
said adjustment member comprising a threaded member threadably engaged with the cap, the threaded member having proximal and distal ends;
the threaded member having a longitudinally extending opening formed therethrough to receive the proximal end of the pull wire, and having a socket formed in its proximal end;
the pull wire having an enlarged retaining member at its proximal end, the retaining member being adapted to be engaged and retained by the socket.

* * * * *